(12) United States Patent
Paladini (10) Patent No.: US 8,831,708 B2
(45) Date of Patent: Sep. 9, 2014

(54) MULTI-MODAL MEDICAL IMAGING

(75) Inventor: Gianluca Paladini, Skillman, NJ (US)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 13/419,574

(22) Filed: Mar. 14, 2012

(65) Prior Publication Data

US 2013/0172739 A1 Jul. 4, 2013

Related U.S. Application Data

(60) Provisional application No. 61/452,809, filed on Mar. 15, 2011.

(51) Int. Cl.
| | | |
|---|---|---|
| *A61B 8/00* | (2006.01) |
| *A61B 6/00* | (2006.01) |
| *A61B 8/08* | (2006.01) |
| *A61N 7/02* | (2006.01) |
| *G01T 1/161* | (2006.01) |
| *A61B 6/03* | (2006.01) |
| *A61B 8/14* | (2006.01) |
| *A61N 7/00* | (2006.01) |
| *A61B 19/00* | (2006.01) |

(52) U.S. Cl.
CPC ....... *A61B 8/4416* (2013.01); *A61N 2007/0052* (2013.01); *A61B 2019/5248* (2013.01); *A61B 2019/5251* (2013.01); *A61B 6/4405* (2013.01); *A61B 2019/5265* (2013.01); *A61B 19/5244* (2013.01); *A61B 19/5225* (2013.01); *A61B 6/4258* (2013.01); *A61B 6/4417* (2013.01); *A61B 6/4458* (2013.01); *A61B 6/481* (2013.01); *A61B 6/5247* (2013.01); *A61B 6/547* (2013.01); *A61B 8/08* (2013.01); *A61B 8/4218* (2013.01); *A61B 8/483* (2013.01); *A61B 8/486* (2013.01); *A61B 8/5261* (2013.01); *A61B 19/2203* (2013.01); *A61B 2019/5276* (2013.01); *A61N 7/00* (2013.01); *A61N 7/02* (2013.01); *G01T 1/161* (2013.01); *A61B 6/037* (2013.01); *A61B 8/145* (2013.01); *A61B 8/4444* (2013.01)
USPC ................ 600/436; 600/439; 600/446; 601/2

(58) Field of Classification Search
USPC ................ 600/436, 439, 446; 601/2
See application file for complete search history.

(56) References Cited

U.S. PATENT DOCUMENTS 4,995,396 A * 2/1991 Inaba et al. .................... 600/431
5,014,708 A * 5/1991 Hayashi et al. ................ 600/436
(Continued)

FOREIGN PATENT DOCUMENTS

EP           1269916 A1 * 1/2003 ............... A61B 8/00
WO   WO 2004042546 A1 * 5/2004 ............... G06F 3/00
(Continued)

OTHER PUBLICATIONS

Wein, Wolfgang et al., "Automatic Registration and Fusion of Ultrasound with CT for Radiotherapy." Proceedings of Medical Image Computing and Computer-Assisted Intervention (MICCAI), Palm Springs, CA (USA), Oct. 2005.

(Continued)

*Primary Examiner* — Long V. Le
*Assistant Examiner* — Angela M Hoffa (57) ABSTRACT

A nuclear probe and ultrasound transducer are interconnected, such as being in a same hand-held housing. The interconnection aligns the coordinate systems in a known spatial relationship. The ultrasound data is used to detect transducer offset or change in position without a tracking sensor. The radiation detected by the nuclear probe may be reconstructed into an image based on the detected transducer position since the nuclear probe moves with the ultrasound transducer. Both anatomical and functional imaging may be provided together without the complications of calibration and tracking. Where a therapeutic transducer is included, therapy may also be provided. The anatomical and functional information identifies the regions for treatment. The same device, already positioned correctly based on the functional and anatomical imaging, is then used for treatment with high intensity focused ultrasound.

8 Claims, 6 Drawing Sheets

(56) References Cited

U.S. PATENT DOCUMENTS

| | | | |
|---|---|---|---|
| 5,655,535 A * | 8/1997 | Friemel et al. | 600/443 |
| 5,823,962 A | 10/1998 | Schaetzle et al. | |
| 6,013,024 A * | 1/2000 | Mitsuda et al. | 600/146 |
| 6,212,423 B1 * | 4/2001 | Krakovitz | 600/473 |
| 6,429,431 B1 * | 8/2002 | Wilk | 250/363.02 |
| 6,631,284 B2 | 10/2003 | Nutt et al. | |
| 6,906,330 B2 * | 6/2005 | Blevis et al. | 250/370.09 |
| 7,094,203 B2 * | 8/2006 | Inoue et al. | 600/439 |
| 7,102,138 B2 * | 9/2006 | Belvis et al. | 250/370.09 |
| 7,652,259 B2 * | 1/2010 | Kimchy et al. | 250/370.08 |
| 7,705,316 B2 * | 4/2010 | Rousso et al. | 250/370.09 |
| 7,872,235 B2 * | 1/2011 | Rousso et al. | 250/363.04 |
| 7,968,851 B2 * | 6/2011 | Rousso et al. | 250/370.09 |
| 8,000,773 B2 * | 8/2011 | Rousso et al. | 600/436 |
| 8,094,894 B2 * | 1/2012 | Nagler et al. | 382/128 |
| 8,423,125 B2 * | 4/2013 | Rousso et al. | 600/436 |
| 8,445,851 B2 * | 5/2013 | Rousso et al. | 250/363.04 |
| 8,489,176 B1 * | 7/2013 | Ben-David et al. | 600/436 |
| 8,521,253 B2 * | 8/2013 | Melman | 600/407 |
| 2006/0184018 A1 * | 8/2006 | Cox et al. | 600/436 |
| 2009/0259123 A1 | 10/2009 | Navab et al. | |
| 2010/0016765 A1 * | 1/2010 | Hall et al. | 601/2 |
| 2010/0266171 A1 | 10/2010 | Wendler et al. | |
| 2010/0290685 A1 | 11/2010 | Wein et al. | |

FOREIGN PATENT DOCUMENTS

| | | | | |
|---|---|---|---|---|
| WO | 2004075987 A1 | 9/2004 | | |
| WO | WO 2004075987 A1 * | 9/2004 | | A61N 7/02 |
| WO | 2004042546 A1 | 5/2006 | | |
| WO | 2008075304 A1 | 6/2008 | | |

OTHER PUBLICATIONS

Wein, Wolfgang et al., "Simulation and Fully Automatic Multimodal Registration of Medical Ultrasound." Proceedings of Medical Image Computing and Computer-Assisted Intervention (MICCAI), Brisbane, Australia, Oct. 2007.

Wendler, T. et al., "Towards intra-operative 3D nuclear imaging: reconstruction of 3D radioactive distributions using tracked gamma probes." Proceedings of Medical Image Computing and Computer-Assisted Intervention (MICCAI), Brisbane, Australia, Oct. 2007.

Wendler, T. et al., "Real-time fusion of ultrasound and gamma probe for navigated localization of liver metastases." Proceedings of Medical Image Computing and Computer-Assisted Intervention (MICCAI), Brisbane, Australia, Oct. 2007.

Node Seeker Brochure from GE Healthcare, 4 pages—downloaded Apr. 15, 2011.

www.surgiceye.com website, 4 pages, downloaded Mar. 8, 2012.

PCT International Search Report mailed Jul. 2, 2012 corresponding to PCT International Application No. PCT/US2012/029203 filed Mar. 15, 2012 (12 pages).

* cited by examiner

MULTI-MODAL MEDICAL IMAGING

RELATED APPLICATIONS

The present patent document claims the benefit of the filing date under 35 U.S.C. §119(e) of Provisional U.S. Patent Application Ser. No. 61/452,809, filed Mar. 15, 2011, which is hereby incorporated by reference.

BACKGROUND

The present embodiments relate to medical imaging. In particular, multi-modal fused visualization of ultrasound imaging and nuclear medicine imaging are provided.

Diagnostic medical modalities, such as computed tomography (CT), magnetic resonance (MR), and ultrasound acquire detailed images. The images depict anatomical structures, such as location of internal organs and tumors. Other modalities, such as positron emission tomography (PET) and single positron emission computed tomography (SPECT), may visualize functional changes or information. PET and SPECT may show areas of cancerous growth or other operation of anatomy, but with less or no details about the surrounding anatomy.

Multi-modal fusion of anatomical and functional information is an effective way to provide greater distinction between physiological (e.g., organ) uptake and pathological (e.g., cancerous) uptake of a tracer. The multi-modal fusion may allow better diagnosis of cancerous masses, particularly in cases where the cancerous tissue is not well delineated in the anatomical images.

The process of fusing such information requires the overlapping images from different modalities to be visualized within a common coordinate system and overlaid or blended together. PET and CT may be combined into one device with know spatial relationship. For both 3D tomography scanning procedures, a patient lies on a motorized bed which moves inside a doughnut-shaped image acquisition device. Both types of images are acquired together in one scanning procedure.

If images are acquired using separate medical devices, calibration and tracking of the devices are used to provide a common coordinate space. Tracking devices (e.g., magnetic or optical sensors) and registration algorithms may be used to compute the proper correspondence between pixels in the respective images. Deformable registration may compensate for deformation and/or distortion and other anatomical changes that may have occurred if the images have been acquired at different times.

Multi-modality fusion based on tracked and registered images is typically a complex and time consuming procedure for the user. Some errors in the registration and tracking process may occur, producing misaligned results. Sometimes registration algorithms fail altogether, particularly when the images being registered together are of modalities that look so different from each other that matching features are difficult to identify.

The fusion of ultrasound with other modalities is challenging. Ultrasound images suffer from speckle noise artifacts and are not easily matched with higher quality images, such as CT or MR scans. For fusion of ultrasound with CT, ultrasound images are simulated from CT scans to find corresponding features in real ultrasound images. Such systems require two separate acquisition procedures to take place and require calibration of a tracking device attached to the ultrasound transducer probe as well as a registration algorithm to compute correspondence between a previously acquired CT scan and live ultrasound images. Such tracking is subject to registration errors.

The small form factor of hand-held transducer probes makes ultrasound an ideal imaging modality for interventional image-guided procedures. In addition to image generation, ultrasound may also be used for non-invasive therapeutic treatment. One ultrasound transducer for combined diagnostic and therapeutic use may be provided. Unfortunately there are still tumors and lesions that are not easily discernable in ultrasound images.

In nuclear medicine, hand-held nuclear activity devices, such as a gamma probe or a beta probe, are capable of detecting the uptake of injected tumor-seeking radiopharmaceuticals. Gamma probes, for example, are used in parathyroid and sentinel lymph node surgery, where the gamma probes provide an audible signal to locate regions where injected radionuclides are present. The locations detected with a gamma probe may be visualized rather than just relying on an audible signal. A tracking system measures the position of data acquired by the gamma probe to compute the images. Such images may then be fused with image data coming from other detectors. For example, images produced with an optically-tracked gamma probe are fused together with images from a video camera calibrated into the same coordinate space. The resulting fused image shows the location of sentinel lymph nodes overlaid onto the patient's skin, providing guidance to surgeons. However, optical tracking has the disadvantage of requiring an un-occluded view of the region of interest by the tracking camera and calibrated marker positions, and suffers from limited accuracy.

For fusing with ultrasound, separate tracking units ensure that the position and orientation of the separate ultrasound and gamma detectors are known. This combined multi-modal fusion of medical imaging data relies on tracking and registration of separate detectors held in place by two hands as part of a complex system requiring careful calibration, accurate tracking, and registration of images acquired by separate medical imaging devices.

BRIEF SUMMARY

By way of introduction, the preferred embodiments described below include methods, systems, instructions, and computer readable media for multi-modal medical imaging. A nuclear probe and ultrasound transducer are interconnected, such as being in a same hand-held housing. The interconnection aligns the coordinate systems in a known spatial relationship. The ultrasound transducer is used to scan and visualize anatomy. The ultrasound data may also be used to detect transducer offset or change in position without a tracking sensor. The radiation detected by nuclear probe may be reconstructed into an image based on the detected transducer position since the nuclear probe moves with the ultrasound transducer. Both anatomical and functional imaging may be provided together without the complications of calibration and/or tracking.

Where a therapeutic transducer is included, therapy may also be provided. The anatomical and functional information identifies the regions for treatment. The same device, already positioned correctly based on the functional and anatomical imaging, is then used for treatment, such as using high intensity focused ultrasound.

In a first aspect, a probe is provided for multi-modal medical imaging. An ultrasound transducer includes a plurality of elements in an array. A nuclear detector is provided for detecting radiation. An interconnection is provided between the ultrasound transducer and the nuclear detector. The interconnection provides common movement of the ultrasound transducer and the nuclear detector during scanning by the ultrasound transducer and detection by the nuclear detector.

In a second aspect, a method is provided for multi-modal medical imaging. A transducer is used to scan a region of a patient with ultrasound. In response to the scanning, ultrasound data representing the region is received. A detector detects radiation with a detector. The detector is spatially integrated with the transducer. /relative motion of the transducer with the ultrasound data is determined. A two or three-dimensional reconstruction of the radiation is produced as a function of the relative motion.

In a third aspect, a system is provided for multi-modality medical operation. An ultrasound array is in a housing. An ultrasound beamformer is connectable with the ultrasound array. The ultrasound beamformer is configured to scan a region of a patient with the ultrasound array and to generate therapeutic high intensity focused ultrasound with the ultrasound array. A nuclear probe connects with or in the housing such that the nuclear probe moves with the housing and ultrasound array. A detector is connectable with the nuclear probe. The detector is configured to detect radiation from the region. A processor is configured to determine locations associated with the detected radiation within the region. The locations are determined as a function of the scan with the ultrasound array. The processor is configured to cause the ultrasound beamformer to focus the therapeutic high intensity focused ultrasound to the locations.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Multi-modality acquisition is performed by a single integrated medical device. The hand-held probe contains both ultrasound transducer elements and one or more nuclear sensors, providing the ability to generate fused anatomical and functional images that better delineate the location of a tumor or lesion not visible with ultrasound imaging alone. Due to the integration, registration of different coordinate systems is not necessary. Data from the ultrasound transducer and from the nuclear activity detector are already within the same frame of reference. Anatomical ultrasound images are fused with functional images, such as PET or SPECT images. Cancerous lesions that are visible based on uptake of radiotracer agents and surrounding anatomy may be identified.

The integrated probe is a real-time acquisition system, as opposed to integrated PET/CT scanners which require several minutes to acquire a dataset. The integrated probe is a compact apparatus compared to a PET/CT scanner, yet retains the ability to generate combined anatomical and functional images. A plurality of arrangements for combined transducer and nuclear detector elements are possible, either with interleaved sensors or side-by-side sensors.

Combined multi-modal image acquisition and therapy may be provided. The integration of therapy may be achieved by using multi-purpose transducer elements, by combining together different transducer elements or by positioning separate imaging and HIFU transducers side-by-side. The single hand-held probe may be capable of transmitting high intensity focused ultrasound (HIFU) pulses for treatment of tumors, lesions, or other undesired tissue structures being imaged. By combining anatomy imaging, function detection, and treatment in a single device with a common frame of reference, cumbersome use of multiple separate devices requiring independent tracking and registration may be avoided. An efficient solution for non-invasive cancer or other condition treatment is provided.

Figure 1:
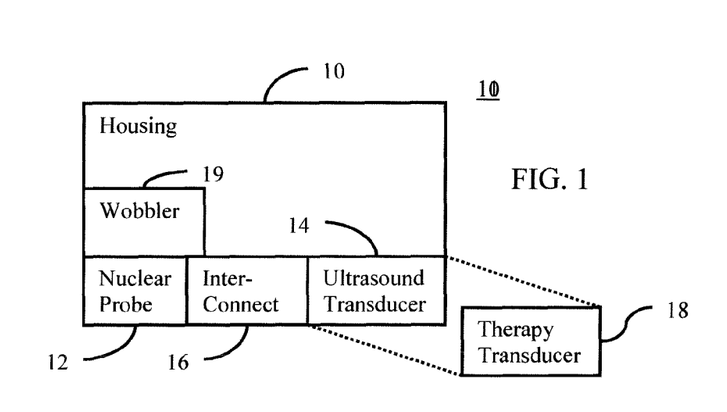
FIG. 1 is a block diagram of one embodiment of an integrated nuclear imaging and ultrasound probe.

FIG. 1 shows a probe 10 for multi-modal medical imaging. The different modes are nuclear imaging and ultrasound imaging. These modes provide anatomical and functional information. The probe 10 may include therapeutic components as well such that one device assists in diagnosis and/or locating of a tumor, cancer, or other region to be treated and also provides treatment.

The probe 10 includes a housing 11, a nuclear probe 12, an ultrasound transducer 14, an interconnection 16, a therapy transducer 18, and a wobbler 19. Additional, different, fewer components may be provided. For example, the wobbler 19 is not provided, or the wobbler 19 or another wobbler connects with the ultrasound transducer 14 as well as the nuclear probe 12. As another example, the therapy transducer 18 is not provided, is the same device (e.g., same array and elements) as the ultrasound transducer 14, or is intermixed with the ultrasound transducer 14. As yet another example, the housing 11 is not provided, such as where the ultrasound transducer 14 and the nuclear probe 12 have separate housings connected together by the interconnection 16.

The housing 11 is plastic, rubber, metal, fiberglass, glass, wood, metal, combinations thereof, or other material for enclosing components. The housing 11 has any shape, such as having a cylindrical region sized and shaped to be held by a hand of a user. The housing 11 may include a grip and/or handle or may itself be sized and shaped for handheld use. A single hand of the user holds the housing 11 for scanning a patient. In alternative embodiments, the housing 11 is larger, such as associated with a larger ultrasound transducer 14 for breast or other larger area imaging. In other alternative embodiments, the housing 11 is smaller, such as being part of an intercavity probe, transesophageal (TEE) probe, or a cardiac catheter.

The nuclear detector 12 and the ultrasound transducer 14 are enclosed within the housing 11. One or more windows, such as through holes, lens, or sections with material transparent to ultrasound and/or radiation, are provided. The housing 11 encloses the other components. In alternative embodiments, the housing 11 includes one or more openings, such as being a frame without cover plates. One or more components may be outside of the housing 11, such as the nuclear probe 12 and part of the interconnection 16 being outside the housing 11.

The ultrasound transducer 14 is in the housing 11. The housing 11 may entirely or only partially enclose the ultrasound transducer 14. The ultrasound transducer 14 is positioned within the housing 11 to allow scanning of the patient.

The ultrasound transducer 14 is a one-, two-, or multi-dimensional array of piezoelectric or capacitive membrane elements. A fully sampled rectangular grid is used, but sparse arrays and/or other grids may be used. The elements are arranged in an N×M pattern. For multi- or two-dimensional arrays, N and M are both integers greater than one. For example, the array is a 1.25D, 1.5D, 1.75D, or 2D array of elements. As another example, a plurality of arrays of elements is arranged together, such as multiple two-dimensional arrays for whole breast scanning.

The ultrasound transducer 14 converts between acoustic and electrical energy. Acoustic energy is used to scan a plane and/or volume. For example, a volume is scanned by sequentially scanning a plurality of adjacent planes with a multi-dimensional array. Any format or scan technique may be used. The scanned volume may intersect or include all of the patient volume.

The therapy transducer 18 is the same device as the ultrasound transducer 14. For example, the same elements are used for diagnostic imaging and therapy. Alternatively, the therapy transducer 18 is a separate device. The dashed lines in FIG. 1 reflect that the therapy transducer 18 may be the same transducer as the ultrasound transducer 14 or a different component. The therapy transducer 18 includes one or more elements, such as a one or multi-dimensional array of elements. Since high intensity ultrasound is used for therapy, the therapy transducer 18 may have active or passive cooling.

The therapy transducer 18 is positioned within the housing 11. For example, the therapy transducer 18 is positioned beside, such as abutting, the ultrasound transducer 14. Alternatively, the therapy transducer 18 is layered along a depth dimension with the ultrasound transducer 14. In other embodiments, the therapy transducer 18 is outside the housing 11, such as being connected with but separate from a diagnostic probe.

The nuclear detector 12 is a gamma, beta, or other probe for detecting radiation. For example, the nuclear detector 12 includes a Geiger-Muller tube or scintillation counter for detecting radiation following interstitial injection of a radionuclide.

The nuclear detector 12 has a single detector and generally pencil shape. Alternatively, an array of detectors may be provided, and/or other shapes may be used.

The nuclear detector 12 connects with or in the housing 11. When the housing 11 and ultrasound transducer 14 move, the nuclear detector 12 also moves. The nuclear detector 12 is adjacent to the ultrasound transducer 14, such as being positioned at an end of an array or adjacent to the array of the ultrasound transducer 14. In one embodiment, one or more elements of a multi-dimensional array are replaced by an end of the nuclear detector 12 such that transducer elements surround the nuclear detector 12 in two dimensions. The aperture formed by the replaced elements may be from a middle of the array or other location.

Figure 3A:
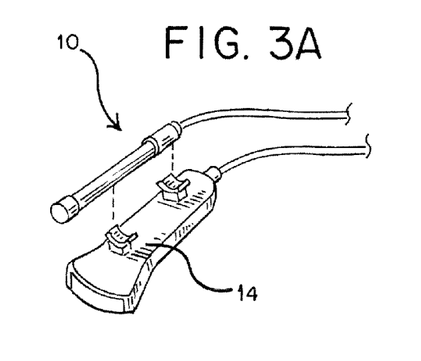
FIGS. 3A-D show examples of different embodiments of an integrated nuclear imaging and ultrasound probe.
Figure 3B:
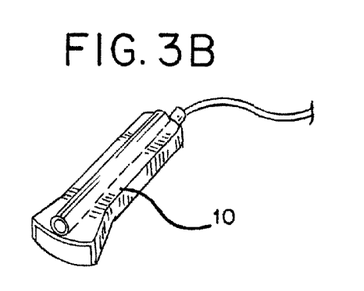
Figure 3C:
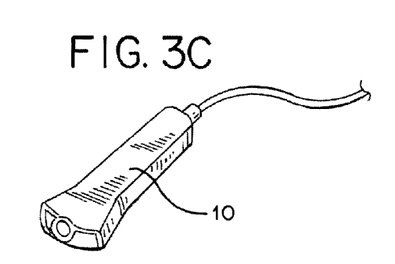
Figure 3D:
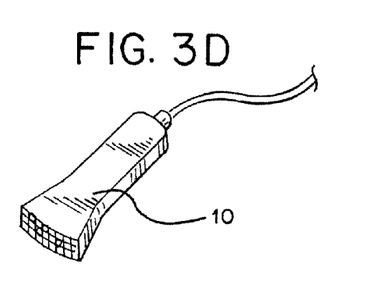

FIG. 3C shows the nuclear detector 12 centered in a one dimensional array of elements of the ultrasound transducer 14. FIG. 3D shows a plurality of nuclear detectors 12 interleaved with a two-dimensional array of elements of the ultrasound transducer 14

The interconnection 16 is the housing 11 itself or other device. The interconnection 16 is the same or different material than the housing 11. The interconnection 16 connects the ultrasound transducer 14 with the nuclear detector 12. By spatially connecting, common movement is provided. The position of the ultrasound transducer 14 relative to the nuclear detector 12 is known. As the ultrasound transducer 14 is repositioned or moved for scanning the patient, the nuclear detector 12 also moves.

In one embodiment, the interconnection 16 is a fixed connection, such as being molded, glued, bonded, riveted, clipped or other attachment of the ultrasound transducer 14 with the nuclear detector 12. The interconnection 16 is direct between the ultrasound transducer 14 and nuclear detector 12. Alternatively, one or more intervening devices are provided, such as arms or ridges connecting the ultrasound transducer 14 with the housing 11, other arms or ridges connecting the nuclear detector 12 with the housing 11, and part of the housing 11 connecting between the two arrangements. FIGS. 3B-D shows the nuclear detector 12 within the housing 11 with the ultrasound transducer 14.

As an alternative to connection within the housing 11, the interconnection 16 of the ultrasound transducer 14 and the nuclear detector 12 is, at least partly, outside the housing 11. For example, a clip or holder is provided for the nuclear detector 12 on the side of a handheld housing 11 for the ultrasound transducer 14. The nuclear detector 12 clips into or connects with the housing 11. FIG. 3A shows an example clip arrangement of the nuclear detector 12 on the ultrasound transducer 14.

As an alternative to a fixed connection, the interconnection 16 is detachable or releasable. A fixed connection provides for set spatial relationship, which may not be changed without destruction or involved disassembly (e.g., mechanical disconnection of parts not intended to be disconnected during use or by a user). The fixed interconnection 16 is fixed relative to ordinary use such that detachment is not intended to occur as part of ordinary operation. For a releasable interconnection 16, a releasable clip or other connection allows separation of the nuclear detector 12 from the ultrasound transducer. 14 by the user.

The interconnection 16 establishes a set or fixed spatial relationship. When attached, the ultrasound transducer 14 is at a known geometric location and direction relative to the nuclear detector. In alternative embodiments, the interconnection 16 is adjustable. A gear, belt, rack and pinion, slider, joint, wobbler, or other device moves the nuclear detector 12 relative to the ultrasound transducer 14. A sensor may detect the relative positions or amount and direction of movement, providing a known spatial relationship.

The interconnection 16 may also connect the therapy transducer 18 with the ultrasound transducer 14. Where separate transducers are used, the interconnection 16 establishes a known spatial relationship between the transducers. For example, a linear array ultrasound transducer 14 connects with the nuclear detector 12, such as within or by the housing 11. The therapy transducer 18 connects adjacent the nuclear detector 12 and/or the ultrasound transducer 14 within or by the housing 11.

The wobbler 19 is a motor, gear, belt, combinations thereof, or other components for moving the nuclear detector 12 and/or the ultrasound transducer 14. For example, the wobbler 19 rocks or sweeps the nuclear detector 12 to detect at different angles relative to the ultrasound transducer 14. The wobbler 19 connects with the nuclear detector 12 such that the nuclear detector 12 tilts at different angles during detection of the radiation. The wobbling may be in one or two dimensions.

Figure 2:
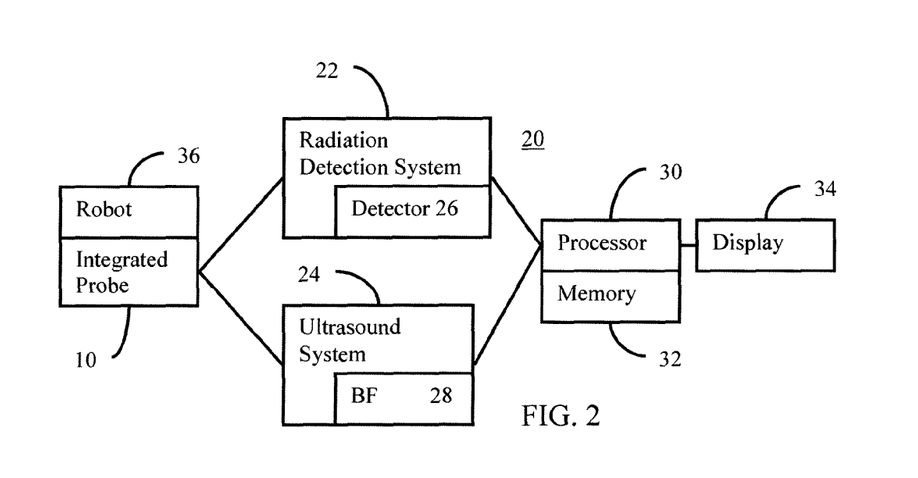
FIG. 2 is a block diagram of an embodiment of a system for multi-modality medical operation.

FIG. 2 shows a system 20 for multi-modality medical operation. The system 11 includes the integrated probe 10, a radiation detection system 22 with a detector 26, an ultrasound system 24 with a beamformer 28, a processor 30, a memory 32, and a display 34. Additional, different, or fewer components may be provided. For example, a network or network connection is provided, such as for networking with a medical imaging network or data archival system. As another example, a preoperative imaging system, such as a computed tomography or magnetic resonance imaging system, is provided. In another example, a user interface is provided. In yet another example, the detector 26 is in the probe 10.

The ultrasound system 24 may be combined with the radiation detection system 22. The two systems 22, 24 may be two separate subsystems within the same housing or be housed separately but with cables or other communications link. Similarly, some of the processing hardware may be shared between the two systems 22, 24. The cables connecting the multi-modal probe 10 to the system 11 may be two cables or one combined cable with two independent channels.

Figure 4:
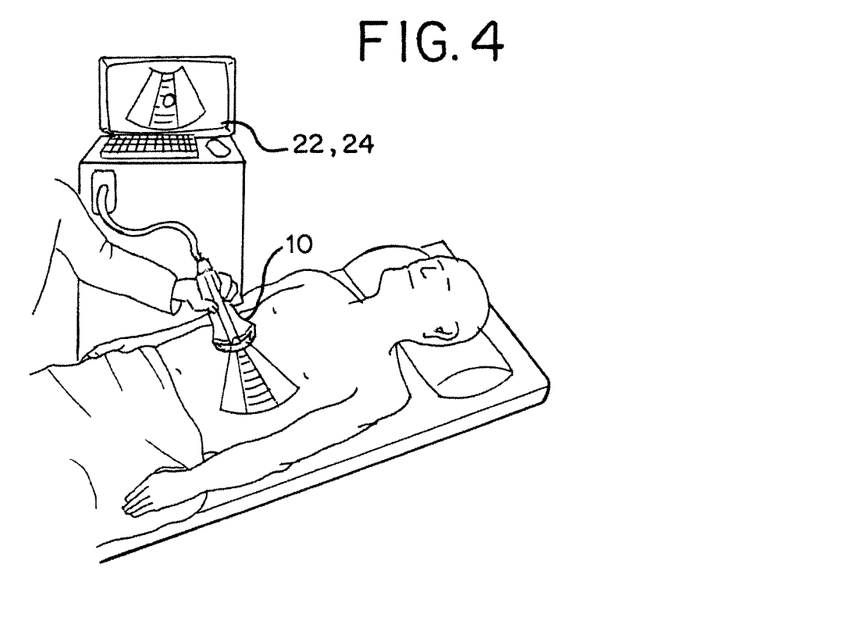
FIG. 4 illustrates use of one embodiment of the system of FIG. 2.

FIG. 4 shows one embodiment of the system in use. The radiation detection system 22 and ultrasound system 24 are integrated together in a cart, cabinet, or other arrangement. The integrated probe 10 connects by a cable to the combined system 22, 24. The gamma probe and ultrasound transducer are combined into a single hand-held device, and ultrasound/nuclear scanner is combined into a system. This arrangement may not require absolute tracking. The image on the screen contains fused information since data is acquired simultaneously from the same frame of reference of the probe. Any relative position information needed to reconstruct 2D/3D SPECT data may be recovered from motion detection in the ultrasound images.

Referring again to FIG. 2, the processor 30 and display 34 are part of a medical imaging system, such as the diagnostic or therapy ultrasound system 24, radiation detection system 22, x-ray, computed tomography, magnetic resonance, positron emission, or other system. Alternatively, the processor 30 and display 34 are part of an archival and/or image processing system, such as associated with a medical records database workstation or server. In other embodiments, the processor 30 and display 34 are a personal computer, such as desktop or laptop, a workstation, a server, a network, or combinations thereof.

The integrated probe 10 connects with both the radiation detection system 22 and the ultrasound system 24. For connection with the ultrasound system 24, a plurality of coaxial cables is provided. For connection with the radiation detection system 22, a single coaxial or other cable is provided. The cables may be within a common cable cover and terminate at a common connector. Alternatively, separate cables are provided from the integrated probe 10.

The connection is fixed or releasable. For example, a connector releasably connects the probe 10 with the radiation detection system 22 and/or the ultrasound system 24. While connections are shown separately to both, the radiation detection system 22 may connect with the ultrasound system 24.

The probe 10 connects with just one of the SPECT or ultrasound systems 22, 24 and the connected system routes the signals as appropriate.

The ultrasound system 24 is a medical diagnostic and/or therapy system. B-mode, Doppler, or other detection is performed on beamformed signals. A scan converter, memory, three-dimensional imaging processor, and/or other components may be provided.

The ultrasound system 24 may be a cart based, handheld, briefcase, or other sized imaging system. The ultrasound system 24 is a stand alone system or may be integrated with the radiation detection system 22, such as sharing a common user interface and/or housing.

The ultrasound system 24 includes the beamformer 28. The beamformer 28 includes transmit and receive channels. The transmit channels generate relatively delayed and apodized waveforms for focusing ultrasound energy along one or more scan lines. The transmit waveforms are applied to the ultrasound transducer for generating acoustic waves. In response to echoes from the transmitted acoustic waves, the ultrasound transducer generates electrical receive signals. The receive channels delay and apodize received signals to sample along the one or more scan lines.

Based on relative delays and apodization, the ultrasound beamformer 28 causes a scan of a region of the patient. The region is a two-dimensional plane. Any scan format may be used, such as linear, sector, or Vector™. In alternative embodiments, the region is a three-dimensional volume. With the transducer in one position, the volume is scanned using mechanical (e.g., wobbler) and/or electrical (e.g., delay) steering of the scan lines (e.g., acoustic beams).

The beamformer 28 may repeat the scanning. Different regions of the patient are scanned as the probe 10 is moved. The regions overlap. The amount of overlap may vary. The amount of overlap depends on the speed of movement of the probe 10, the amount of time to scan, and the scan pattern.

The transmit channels of the beamformer 28 may include amplifiers or waveform generators sufficient to generate high intensity focused ultrasound. Acoustic energy with greater amplitude and/or longer duration is generated for therapy. A larger aperture, greater number of cycles and/or greater waveform amplitude as compared to use for diagnostic imaging may be used to generate acoustic energy sufficient to increase the temperature of tissue. The therapy waveforms are focused so that the therapy is applied at desired locations with less acoustic amplitude at other locations.

The radiation detection system 22 is a circuit, processor, display and/or other components for receiving detected radiation information. The radiation detection system 22 includes the detector 26. Radiation signals (e.g., gamma rays) from the probe 10 are sent to the detector 26 for conversion to electrical energy. Alternatively, the detector 26 is part of the probe 10.

Figure 5:
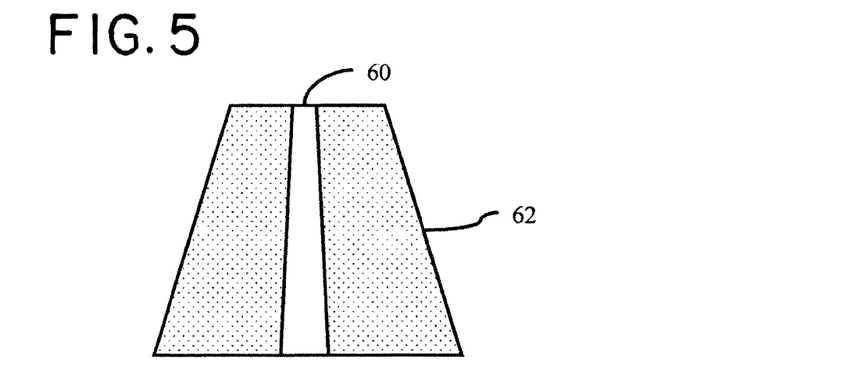
FIG. 5 is a graphical representation of example scan and detection regions.

The detector 26 detects radiation from the region. Radionuclides emit gamma radiation or emitted positrons cause release of gamma radiation. The detector 26 detects the radiation. The detector 26 and/or the probe 10 are directional. Radiation emitted from within a cone shaped region extending from the radiation detector 12 of the probe 10 is detected. FIG. 5 shows a planar ultrasound scan region 62 with a cross-section of the cone region 60 for radiation detection. Other relative sizes may be provided. As a single element, depth is not detected. Readings are taken for each position of the probe 10 as the probe 10 is moved, providing a projection type, two-dimensional sampling of the radiation over a three-dimensional volume. Where an array of detectors is used, depth information may be received. Where the single element is tilted at different angles and the probe 10 is moved, the radiation distribution in three-dimensions may be measured.

In one embodiment, the radiation detection system 22 includes a computer for reconstructing the radiation detected at the probe 10. The radiation detection system 22 is a standalone device, such as a full SPECT system, a PET system, a workstation, or a computer. Alternatively, one or more processors of the ultrasound system 24 perform the reconstruction without other devices. The radiation detection system 22 may be implemented in the processor 30 without a separate device. If 2D or 3D SPECT or PET reconstruction is used, multiple ultrasound images are acquired from different directions or orientations. The ultrasound images are acquired together with the corresponding 1D readings from the nuclear probe 10. A relative motion path is determined, such as determining by analyzing similarities in the multiple ultrasound images or by using a relative motion sensor such as an accelerometer or gyroscope. The relative motion path is used to determine the orientation of the 1D readings from the nuclear probe 10 with respect to each other, in order to perform a SPECT (based on a gamma probe) or PET (based on a beta probe) reconstruction. Absolute tracking, such as tracking with a magnetic position sensor attached to this multi-modal probe 10, may be used with or instead of relative motion.

Accuracy of SPECT reconstruction may depend on the number of acquired images and their orientation. Reconstructed SPECT results from the freehand probe 10 may be registered with more accurate images from a 3D SPECT dataset acquired prior, as a pre-operative scan, to using the system 11.

The processor 30 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for determining position and/or generating images. The processor 30 is a single device or multiple devices operating in serial, parallel, or separately. The processor 30 may be a main processor of a computer, such as a laptop or desktop computer, or may be a processor for handling some tasks in a larger system, such as in an imaging system (e.g., radiation detection system 22 or ultrasound system 24).

The processor 30 determines locations associated with the detected radiation within the region. The radiation detection system 22, through the detector 26, outputs measurements of radiation at different positions of the probe 10 relative to the patient.

The processor 30 determines the relative positions of the probe 10 using the ultrasound data. Since the location of the detector 12 and the corresponding measurement region of the detector 12 are known in relation to the ultrasound transducer 14, determining the relative locations of the ultrasound transducer 14 provides the relative locations of the radiation detector 12 for reconstruction.

As the probe 10 is moved or moves, the ultrasound transducer 14 is used to scan the patient. The nuclear detector 12 also detects. The scanning and detection occur with the probe 10 in different positions. The probe 10 is held stationary or continues to move during the detection and scanning. Rather than determine an absolute position in world coordinates, the relative position between different scans is determined. Relative motion between scans indicates the spatial positioning relative to each other of the detected radiation.

The ultrasound data representing the patient from different positions of the ultrasound transducer 14 is correlated. The processor 30 registers the ultrasound data from one scan with ultrasound data from another scan. A level of similarity between the ultrasound data of different scans is identified. Similarity is determined using a correlation, such as a minimum sum of absolute differences, cross correlation, autocorrelation, or other correlation. For example, a two- or three-dimensional set of data is translated and/or rotated into various positions relative to another set of data. The relative position with the minimum sum or highest correlation indicates a match, alignment, or registration location.

Figure 6:
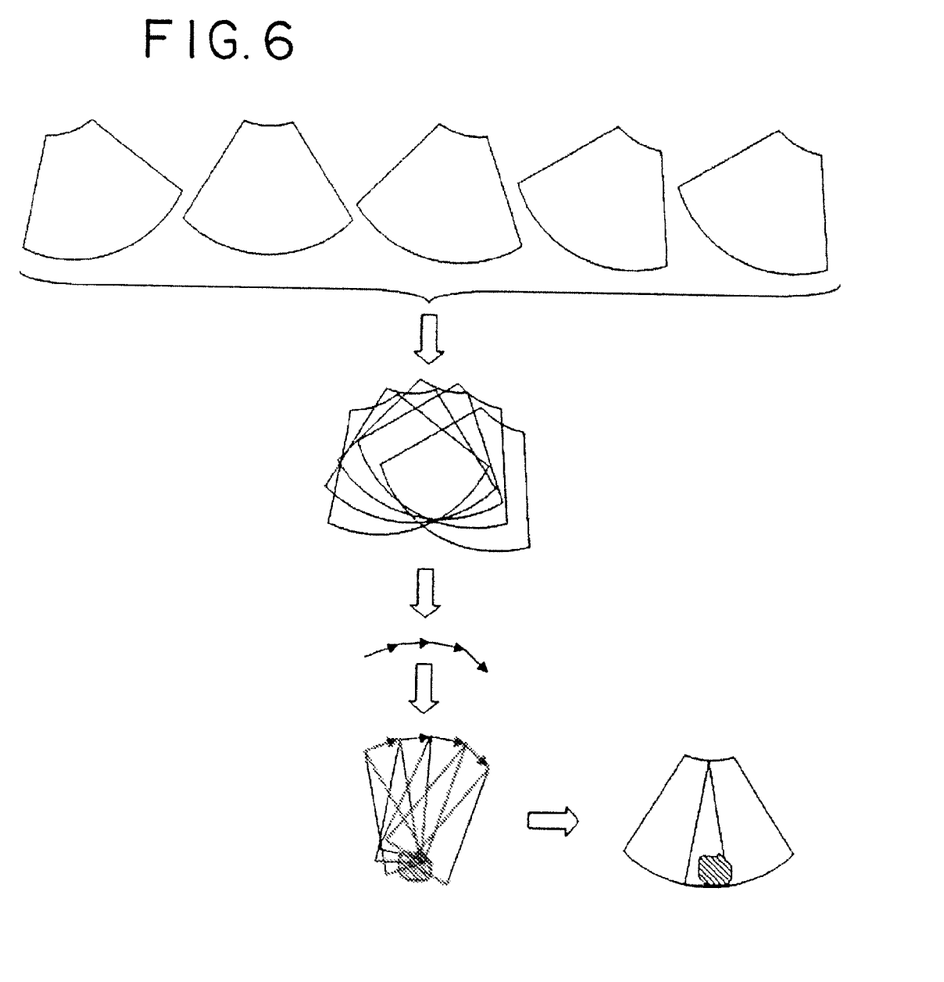
FIG. 6 illustrates acquisition and combination of imaging information.

FIG. 6 represents acquisition of the different component frames of data, then alignment to determine motion associated with the probe 10, use of the motion to spatially align readings from the nuclear detector 12, and combination of the nuclear data with an ultrasound image. Motion detection in ultrasound images is used to recover a relative motion path. This motion path is used to determine the corresponding relative motion of the integrated gamma probe. The motion may be used for 2D/3D SPECT reconstruction and identification of a cancerous lesion. Absolute tracking is not necessary. A path with the same shape may be oriented vertically or horizontally with respect to an absolute coordinate system. For reconstruction, the relative orientation is used.

The similarity may be determined using full sets of scan data or may use sub-sets, such as a region of interest or a decimated set. A same set of scan data may be used as a reference set for comparing with the scan data of all or multiple of the scans. Alternatively, scan data at one time is compared to scan data from the immediately prior or subsequent scan in a moving window. The data to be compared may be filtered or otherwise processed to enhance speckle or features while removing or reducing features or speckle. Alternatively, unfiltered or not processed scan data is used.

The similarity may be based on imaged features. Image processing may identify features. The user may identify features. Identifying three or more features or one or more features with a corresponding orientation represented by both data sets indicates relative positioning of the patient volume and the scanned volume. Alternatively, the similarity is based on speckle pattern. Speckle pattern and features may be used together for measuring similarity, such as providing correlation of data sets without filtering or isolation of features.

The relative positioning indicates a translation and/or rotation of one set of data relative to another set of data. The coordinates of the different volumes or planes may be aligned or transformed such that spatial locations in each set representing a same tissue have a same or determinable location.

The processor 30 determines the locations of the detected radiation based on the relative displacement shown by correlation of ultrasound data. The correlation allows the reconstruction of radiation sources in the region.

The processor 30 may also be configured to cause the ultrasound beamformer 28 to focus therapeutic high intensity focused ultrasound to one or more locations. The reconstruction of the detected radiation may indicate one or more locations for treatment. After confirming the region to be treated based on the diagnostic and/or functional imaging, the locations are treated with ultrasound. Since the same transducer or transducer with a known spatial relationship to the therapy transducer is used, the treatment may occur without further calibration.

The processor 30 may combine data. For example, data from different scans is compounded to represent an extended region. The extended region is greater than obtainable with the transducer 14 scanning from one position. The data may be normalized or filtered to remove the effects of compounding different amounts of data where some regions have different numbers of scans covering the region. Spatially aligned data may be combined by summing, averaging, alpha blending, maximum selection, minimum selection or other process. Alternatively, separate images are generated for each scan or for a representative scan.

The processor 30 may combine functional and diagnostic information. For example, the functional information is represented by a color or graphic overlay. Locations associated with detected radiation above a certain amount are highlighted in the diagnostic image.

The robot 36 includes one or more arms and joints. The robot 36 connects with the ultrasound transducer 14 and the nuclear probe 12 by connection with the housing 11. Alternatively, separate arms or parts of the robot 36 hold and position the ultrasound transducer 14 and the nuclear probe 12.

An active robot 36 may be used, such as including sensors, motors, and controllers for positioning the probe 10 by the robot 36. The robot 36 positions the housing 11 at different positions relative to the patient. For radiation detection, the positions may be spaced slightly away from the patient. For ultrasound scanning, the positions may be against the patient. The relative position of the probe 10 may be indicated by the robotic sensors instead of or in addition to the comparison of scan data.

In alternative embodiments, the robot 36 is a passive assist system. Motors, sensors and controllers may or may not be provided. For example, resistance devices, springs, pneumatics or other loading devices hold the probe 10 wherever a user positions the probe 10 and robot 36. As another example, the user positions the probe 10, but one or more sensors and motors may be used to automatically move the probe 10 away from a patient or to press the probe 10 against the patient for ultrasound scanning.

Figure 7:
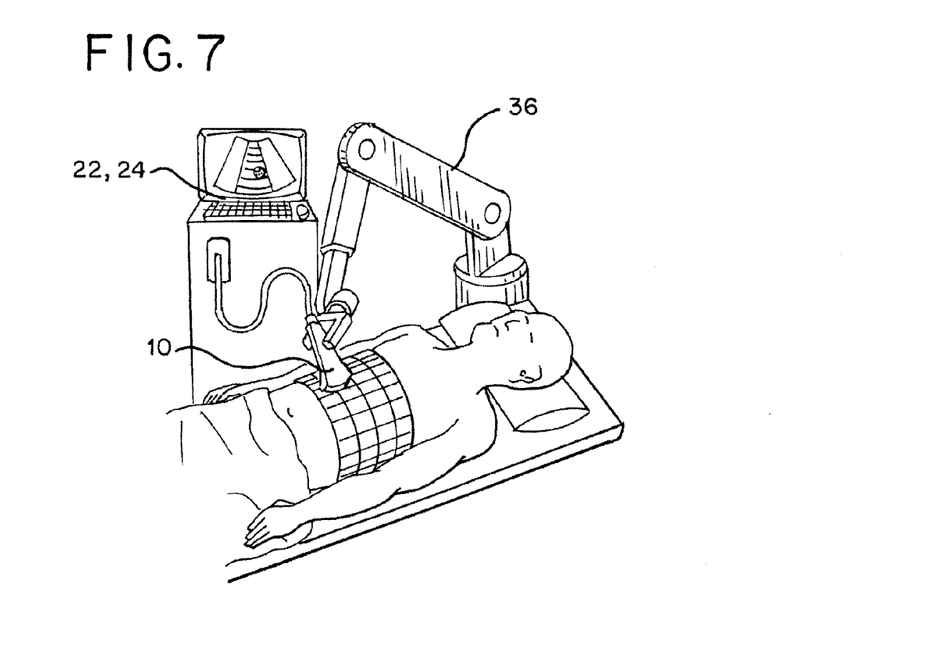
FIG. 7 illustrates use of a robotic embodiment of the system of FIG. 2.
Figure 8:
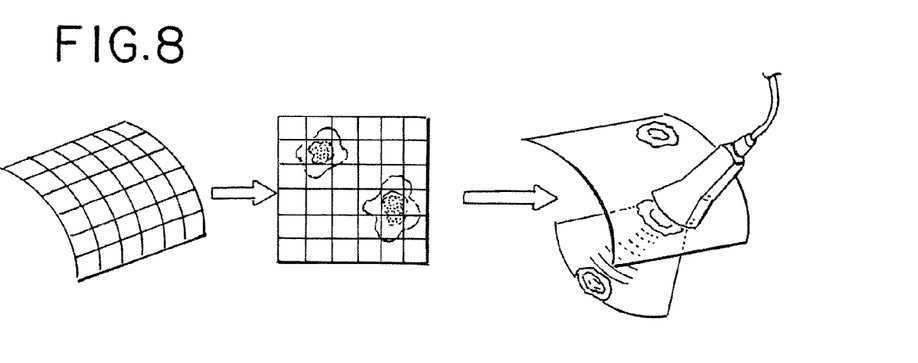
FIG. 8 illustrates a grid pattern and scanning using the robotic embodiment of FIG. 7.

FIG. 7 shows an example use of the integrated probe 10 with the robot 36. A robot arm controls the scanning sequence. FIG. 8 is an illustration of an example scan pattern used by the robot 36. A first pass is made along a grid pattern. The grid is shown as curved, such as associated with an outside surface of the patient. Other surfaces may be used. A resulting 2D map is created, where 'hotspots' (areas of higher nuclear activity) may be easily identified. In a second pass, the robot 36 positions the probe 10 over each hotspot and moves the probe 10 according to a more localized (e.g., higher resolution and/or readings from different directions or angles) scanning protocol in order to reconstruct the underlying 3D lesion.

In one example embodiment, the probe 10 is mounted onto an articulated robot arm rather than being used free-hand. The probe's motion trajectory may be planned and known upfront, rather than being computed from freehand motion subject to inaccuracies. Fully-automated scanning and/or treatment may be provided. For example, in a first pass, the robot arm moves the integrated probe 10 by hovering over the patient in a pre-defined pattern, without needing to touch the patient's skin. The integrated probe is moved over a motion path that can be used to produce a 2D and/or 3D SPECT reconstruction. A 2D map of locations of higher radionuclide uptake ("hotspots") are detected and visualized. Then, the arm positions the integrated probe on the patient's skin at the location of each detected hotspot with the help of force-feedback sensors. An optional registration step with pre-acquired 3D PET/SPECT (such as 1D-3D registration between 1D gamma readings and pre-operative 3D SPECT data) may further enhance the reconstruction results. Then, HIFU may be directed to the location of the detected regions in order to non-invasively treat the affected areas. Further radiation detection and/or diagnostic scanning may confirm proper placement before treatment. Any of these steps may be performed manually by a human operator, or the same may be performed by any combination of robot-assisted and human-assisted steps.

In one embodiment, radiation data from the probe readings is registered with pre-operative 3D SPECT or PET data. This correlation occurs without first reconstructing the radiation data from the probe. Where the probe is not as accurate as currently available 3D PET/SPECT scanners, registration of the radiation data or reconstruction and then registration of the reconstructed radiation data with pre-operative data may provide increased accuracy. The data acquired by the nuclear probe is registered with pre-operative PET/SPECT scans, either by using directly 1D data from the nuclear probe or by first doing an approximate 2D or 3D reconstruction.

In an alternative embodiment, one or more absolute and/or relative position sensors are provided. A magnetic tracking sensor, camera-based sensor, accelerometer, gyroscope, or other sensor determines a position or the change in position of the probe 10 at different times. The relative or absolute position information is used instead of or in addition to the ultrasound data to determine the locations of the functional information. The sensor or sensors may be used to locate the positions of scans from the ultrasound transducer 14 and/or nuclear probe 12. The locations of functional information from different times are determined for generating an image. The sensor or sensors may be used to locate the position of different scans in three-dimensions for reconstruction of data into a three-dimensional grid.

The memory 32 is a graphics processing memory, a video random access memory, a random access memory, system memory, random access memory, cache memory, hard drive, optical media, magnetic media, flash drive, buffer, database, combinations thereof, or other now known or later developed memory device for storing data or video information. The memory 32 is part of an imaging system, part of a computer associated with the processor 30, part of a database, part of another system, or a standalone device.

The memory 32 stores one or more datasets representing two or three-dimensional patient regions. The ultrasound scan data is stored. Ultrasound data from different scans with the probe 10 at different locations is stored for determining relative position of the probe 10. The detected radiation data is stored, both before and after reconstruction.

Other types of data may be stored, such as pre-operative diagnostic scan data (e.g., ultrasound, x-ray, computed tomography, magnetic resonance, or positron emission). For example, CT or MRI data is acquired prior to intervention, such as just prior to (same day) or during a previous appointment on a different day. The data represents tissue, preferably in a high resolution.

The data is interpolated or converted to an evenly spaced three-dimensional grid or is in a scan format. Each datum is associated with a different volume location (voxel) or area location (pixel) in the patient region. Each location is the same size and shape within the dataset, but may represent different sized volume or area locations.

The memory 32 or other memory is a non-transitory computer readable storage medium storing data representing instructions executable by the programmed processor 30 for multi-modality medical imaging. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multi-processing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 34 is a monitor, LCD, projector, plasma display, CRT, printer, or other now known or later developed devise for outputting visual information. The display 34 receives images, graphics, or other information from the processor 30, memory 32, ultrasound system 24, or radiation detection system 22.

The display 34 provides one or more images representing anatomy and/or function. The images may be a combination of multiple sources of information, such as representing anatomy highlighted in color based on function. The images are reconstructed planar images from a scanned volume, are two-dimensional planar images as scanned, and/or are three-dimensional renderings to the display 34. Preoperative images may be generated for simultaneous display. Alternatively, the positions represented by the preoperative images are registered with the ultrasound scan and/or functional data. The functional information may be overlaid on the preoperative data with or without ultrasound information.

Figure 9:
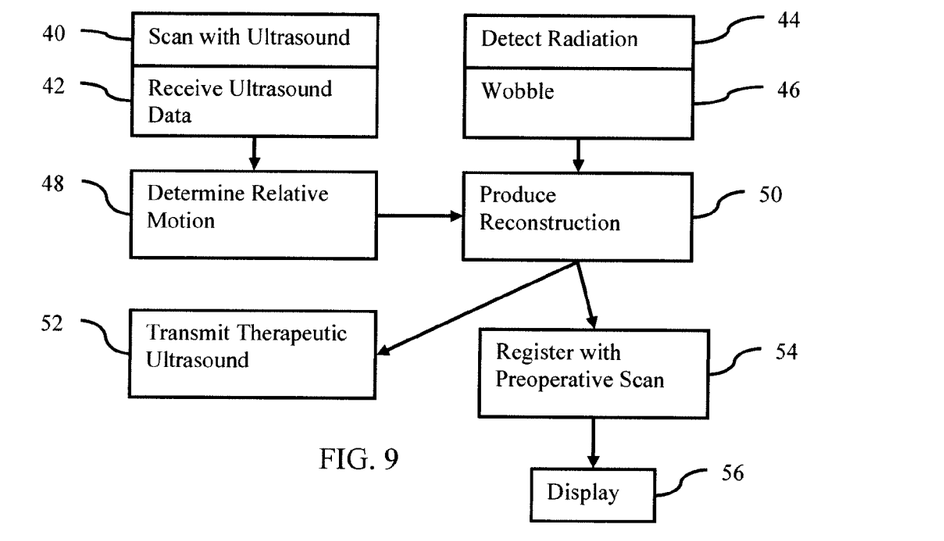
FIG. 9 is a flow chart diagram of one embodiment of a method for multi-modality medical operation.

FIG. 9 shows a method for multi-modal medical imaging. The method is implemented by the probe 10 of FIG. 1, the system 20 of FIG. 2, the probes of FIGS. 3A-D, the system of FIG. 4, the system of FIG. 7, or another system 20 or probe 10. The acts are performed in the order shown or other orders. Acts 40 and 44 may be performed at a generally same time or sequentially. Additional, different, or fewer acts may be provided. For example, the display act 56 is not provided, but instead the reconstruction is used to control therapeutic scanning. The registration with preoperative data of act 54 is optional. As another example, user input is provided for selecting display, controlling combination, controlling registration, or other purposes. In another example, the transmission of therapeutic ultrasound in act 52 and/or the wobbling in act 46 are not provided.

In act 40, a region of the patient is scanned with ultrasound. A transducer converts electrical waveforms into acoustic energy focused at different locations in a two or three-dimensional scan pattern. The same region (e.g., transducer at the same position) may be scanned once or multiple times.

The transducer is moved, allowing scanning from different positions. Different regions of the patient are scanned. The regions overlap. One or more scanned regions may not overlap, such as sequentially scanned regions overlapping but with sufficient movement that the beginning and ending scans do not overlap.

Any scan pattern or format may be used. The scanning is for diagnostic imaging of the patient anatomy or fluid. For example, B-mode or Doppler scanning is used. Parametric imaging may be performed, such as elastography, strain, or shear. One or more acoustic beams are formed along each of a plurality of scan lines during a scan sequence. Each transmission may form one or more acoustic beams. The acoustic beams may be focused or may be planar waves (e.g., infinite focus or diverging wavefront).

In act 42, ultrasound data is received in response to the scanning. The scanning is performed in the acoustic domain. The acoustic echoes are transduced into electrical signals. The electrical signals are beamformed or otherwise transformed into samples from different locations in the scanned region. The electrical signals are processed as ultrasound data. The ultrasound data is at any stage of processing, such as beamformed signals before detection, detected or estimated signals before scan conversion, scan converted signals before display, or displayed data.

The ultrasound data represents the scanned region. For a two-dimensional or planar scan, the ultrasound data represents the plane. The plane may be skewed due to motion of the transducer, but is still generally planar due to the speed of scanning. For a three-dimensional or volume scan, the ultrasound data represents voxels distributed in the three-dimensions. The ultrasound data may be scan converted or changed from a scan format to another format, such as a regularly spaced three-dimensional grid or a Cartesian coordinate format.

In act 44, radiation is detected. Radionuclides, radioactive tracer, or other sources of radiation in the patient generate positrons or gamma rays. A detector senses the gamma rays or other radiation. The sources of radiation are taken up, transferred, or pooled, showing the function of anatomy. For example, the amount of tracer taken up by brain tissue indicates the functioning of the brain tissue. As another example, distribution of the tracer in the cardiac system shows operation of the cardiac system. In other embodiments, the tracers are tagged to bind to or otherwise collect based on function. For example, the radionuclides bind to cancer or show glucose uptake. Any now known or later developed functional imaging may be used.

The detector is spatially integrated with the transducer used for scanning in act 40. Spatial integration provides for the detector to move with the transducer and to be at a known or measureable relative location. The angle and translation of the detector relative to the transducer is fixed or adjustable. Spatial integration may be provided by attaching, enclosing, connecting, or otherwise spatially fixing, at least temporarily, the detector with the transducer.

The level or magnitude of radiation at different locations is detected. The detector detects radiation along a line, such as a cone shaped region extending from the detector. As the detector moves, the radiation at different locations is measured. The measurements provide a two-dimensional map of radiation emitted in a projection along a third dimension or a one-dimensional map of radiation emitted in a projection along a plane.

In act 46, the detector is wobbled. Wobbling tilts the detector so that, with translation movement of the detector, any given location (e.g., voxel) is measured from different angles. With rocking or tilting of the detector, measurements for projections through the same volume, but at different angles, are obtained. These measurements may be converted into a three-dimensional map of radiation emission, providing measurements in three-dimensions instead of projections along one or two dimensions.

The wobble or tilting is provided by a motor and gearing. Belts with guides or other mechanism may cause the detector to tilt to different angles. The tilting varies over time, such as rocking the detector in a cyclical pattern. The tilt angle is known based on timing and/or measured, such as using an encoder, optical sensor, or other sensor.

With or without wobbling, the detector and the transducer are moved to different locations. The movement is performed by the user, such as grasping a probe with one hand and translating and/or rotating the probe. The movement is alternatively performed by a robot. Any movement pattern may be used, such as translating a three-dimensional scanning transducer along a line while the detector is rocked in a plane orthogonal to the line during the movement along the line. Two or three-dimensional movement patterns may be used.

FIG. 6 shows movement of the transducer to acquire frames of data (represented as Vector® scan areas). The different scans are shown separately, and the resulting overlapping of the scan areas is also shown. As indicated by the arrows, the transducer moves to different locations to scan the respective overlapping areas.

In act 48 of FIG. 9, relative motion of the transducer is determined. FIG. 6 shows the relative motion as the arrows or vectors corresponding to movement of the transducer for scanning the overlapping areas. Relative motion is motion or displacement from one location to another. Absolute motion or positioning within a patient or world frame of reference is not determined. Alternatively, absolute position or motion is determined using a magnetic position or optical sensor. Calibration is performed for such sensors for aligning to the world or patient coordinate system.

The relative positions are determined with the ultrasound data. The ultrasound data is associated with scans with the transducer at different locations. The ultrasound data from different scans is correlated. For example, the ultrasound data from a first scan is correlated with the ultrasound data from a second scan. The ultrasound data from a third scan is correlated with the ultrasound data from the second scan. For a most recently acquired set of ultrasound data, the next most recently acquired set of ultrasound data is used for correlation. The reference for each correlation shifts over time. Every other or other groupings of scans may be used for correlation. Alternatively, the ultrasound data from one scan is used as the reference for any of the other sets of ultrasound data.

The correlation is along a line, in a plane, or in a volume. The correlation may alternatively or additionally be over one to three axes of rotation. Different translations and/or rotations between the sets of data are searched and a corresponding similarity value is calculated. The translation and/or rotation combination with the highest or sufficient correlation indicates spatial alignment showing the relative motion. Any search pattern may be used, such as numerical optimization, course-to-fine searching, subset based searching, or use of decimated data.

The correlation may be based on all of the data in the sets. For example, speckle is maintained in the ultrasound data and used for correlation with or without anatomical information. The correlation may be a function of at least one feature. For example, the user or a processor identifies features in each data set. The features may be tissue boundaries, tissue regions, bone region, fluid region, air region, combinations thereof, or other feature. The data representing the features with or without surrounding data is used for the correlation. The features may be identified in one set (e.g., ultrasound) for matching with all of the data in another set, or features of one set may be matched to features of another set.

The data may be used for correlation without alteration. In other embodiments, one or both sets of data are filtered or processed to provide more likely matching. For example, the ultrasound data is low pass filtered, decimated, or image processed.

For each position of the transducer, a difference in position from another position is provided. The translation and/or rotation indicate relative position or motion. Since the transducer and detector are spatially integrated, the same translation and/or rotation apply to the detector. Using the known spatial relationship of the detector to the transducer, the detected radiation may be positioned in the ultrasound coordinate space.

In alternative embodiments, an absolute position sensor or sensors or relative position sensors are used to determine the position of the transducer. Magnetic position sensors may be used to determine absolute position. Accelerometer or gyroscope may be used to determine relative position.

In act 50, the radiation distribution is reconstructed. The reconstruction is a tomographic reconstruction and/or is based on relative positioning of detected radiation from different times and/or locations. The reconstruction may be one or two-dimensional. The detector is moved in a plane or along a curved surface. For each sample location along the plane or surface, a measurement of radiation along an orthogonal line is made. As shown in FIG. 6, the radiation is detected along triangular or cones extending from the detector. The radiation is shown as being from a irregular region, represented as generally circular with diagonal lines. Using the relative positions determined from the ultrasound data or sensor and/or the absolute positions determined from the sensor, the relative position of each measurement is provided. The relative position of the measurement lines or regions is mapped. A regular sampling may be interpolated. A two-dimensional reconstruction is provided where the magnitude at each location represents the radiation along an orthogonal line and the probe is moved in two dimensions.

Since a nuclear activity probe produces a one-dimensional reading, the probe's motion is used to reconstruct either a 2D or a 3D SPECT image from the data acquired by the detector. Motion estimation for the single integrated ultrasound/nuclear probe is simplified because relative motion between ultrasound images is used instead of tracking. Computing the motion occurring between partially overlapping ultrasound images is simple, since the images being correlated are of the same modality. Without using any tracking system, several ultrasound images are acquired. Motion estimation and/or image registration algorithms compute the relative motion that took place between each acquired image. Such motion information may be directly utilized for SPECT reconstruction of nuclear data from the integrated nuclear probe, since nuclear data is acquired within the same frame of reference as the ultrasound images. FIG. 6 shows the completion of an image region with the reconstructed radiation region. The complete radiation region may be provided for any of the component scans or frames of data.

In one embodiment, a three-dimensional reconstruction is provided. As the detector is translated, the detector is also tilted to different angles. As a result, depth information may be derived. Each voxel location contributes to measurements by the detector at different times. These locations are distributed in three-dimensions in the volume. The tilt angles for the measurements and position information may be used to reconstruct the distribution of radiation. Any tomographic reconstruction process may be used, such as filtered back projection or iterative reconstruction.

In one embodiment, 3D SPECT reconstruction is provided. The integrated ultrasound/nuclear probe contains a 3D ultrasound transducer, generating 3D ultrasound data. The 3D ultrasound data from different scans are registered together in order to compute relative motion. The relative motion is used to reconstruct 3D SPECT images from the detected radiation.

The nuclear activity detector itself may be mechanically steered within the integrated probe housing in order to produce multi-dimensional readings, which are combined with the estimated motion of ultrasound data in order to compute 2D/3D SPECT reconstruction.

The relative motion is determined in act 48 and the reconstruction is produced in act 50 without tracking the detector and the transducer with a sensor external to the detector and the transducer. Optical, magnetic position, or other sensors to determine the position of the probe relative to the sensor frame of reference is not needed. Absolute position determination is not needed. For relative positions, the complication of an additional sensor may be avoided. As a result, the calibration for registration based on an external position sensor may be avoided. Relative position is determined without calibrating a position sensor. Not requiring any separate tracking system may be an advantage. Overall equipment cost and setup time is reduced.

In other embodiments, a tracking system, such as magnetic tracking, may be used. The tracking system may improve accuracy or allow operation, especially in cases where the acquired ultrasound images do not properly overlap or contain shadowing and/or other ultrasound artifacts. Even with a separate tracking system, no calibration and absolute position tracking with respect to the region of interest being scanned is needed for SPECT reconstruction. Since the reconstruction uses relative motion between ultrasound images, tracking absolute motion with respect to the region being scanned is not used.

In an alternative embodiment, absolute position sensing or tracking is used. Since the nuclear detector and the transducer are integrated, only one such sensor or tracking device is needed for both. Additional external instruments may be tracked with respect to the fused ultrasound/SPECT data. For example, a surgical instrument is tracked. The absolute position sensing may be used for registering the ultrasound and/or SPECT reconstruction with other imaging data, such as preoperative MR or CT scans.

In act 52, therapeutic ultrasound is transmitted. Therapeutic ultrasound has a frequency, amplitude, duty cycle, number of cycles and/or other characteristic to cause tissue to increase in temperature or to cause cavitations. For example, a focal region is subjected to a mechanical index over 1.5 for tens, hundreds or thousands of cycles of a waveform in the kilo or megahertz range.

In one embodiment, pulses of high intensity focused ultrasound (HIFU) are used to treat cancers, tumors, lesions, or other undesired tissue structures. HIFU energy heats an area of focus sufficiently to necrotize the undesired tissue, while avoiding harm to healthy tissue.

The transducer used for imaging or a different transducer transmits the acoustic energy to locations in the reconstruction associated with the radiation. A therapy element or array of elements is used to generate acoustic energy. Using an array, lens, shaped element, or combinations thereof, the acoustic energy is steered to the region or regions to be treated. The functional information from the detected radiation indicates the locations for treatment.

The user may reposition the probe and verify the location of the region to be treated. The verification is made by aligning features or anatomy using the ultrasound data. A degree of similarity may be calculated and output to the user to verify proper positioning. The radiation may be measured again for additional or different verification. Alternatively, the radiation is not measured again. The previous reconstruction aligned with the ultrasound data is used to identify the anatomy and location for a current treatment.

The ultrasound transducer may be used after or during therapy to determine the results of the therapy. For example, strain, shear, or elastographic imaging is performed. Tissue properties are detected with ultrasound. The tissue properties may indicate the health or effects of treatment of tissue.

The diagnostic imaging, detecting anatomy function, and treating may be performed with the transducer, the detector, the therapy element in a common housing. The therapy element may be part or all of the ultrasound transducer used for diagnostic imaging or correlation. By providing the common housing or other spatial integration, reconstruction to identify locations to be treated and treatment are provided with one device. Due to the spatial integration, the functional imaging, anatomic imaging, and therapy may be provided without calibration or other complex set up process. The user merely starts scanning the patient. After moving the transducer to different locations, functional information integrated with anatomy information is provided to the user and/or used to then treat the patient.

In act 54, the reconstruction of the radiation distribution is registered with a preoperative scan of the region. The accuracy of SPECT reconstruction from real-time data acquired from the integrated ultrasound/nuclear probe may be limited by the number and diverse orientations of multiple images being acquired and motion correlated. Preoperative MR and/or CT data may be registered with the ultrasound data. For example, separately pre-acquired CT datasets are fused with the functional reconstruction and/or the ultrasound data using position sensing. The ultrasound data is aligned to the coordinate system of the CT dataset by coordinate conversion through a sensor coordinate system. Alternatively, simulated ultrasound images are computed from CT scans. Corresponding features in real ultrasound images and the simulated images are aligned. The alignment provides a registration between the coordinate systems. The SPECT data from the integrated probe may be overlaid with CT.

Real-time 2D/3D SPECT from the integrated probe may be fused with pre-acquired PET and/or SPECT datasets from 3D tomographic scanners. This may be useful in order to get a better delineation of lesions, by matching approximate SPECT reconstructions from the real-time integrated handheld probe with accurate PET/SPECT reconstructions from 3D tomography.

In act 56, one or more images are displayed. The reconstruction is displayed as a two-dimensional image. Alternatively, the image is rendered from voxels of a three-dimensional reconstruction. The images represent spatial distribution of the detected radiation. Any functional imaging may be provided.

An ultrasound image or images may be displayed. Two-dimensional or three-dimensional imaging is provided. The ultrasound image may represent an extended field of view where data from different scans is combined. Different scans represent overlapping fields of view. By combining the overlapping fields of view, the extended field of view is provided.

The radiation distribution may be overlaid or combined with the ultrasound image. For example, the ultrasound image is a grayscale, B-mode image. The radiation magnitude is mapped to color such that different colors, hues, or brightness represent different magnitudes. The color information modulates the grayscale image. Alternatively, the radiation reconstruction is displayed as a separate image, but adjacent to the ultrasound image. A graphic indicating the spatial relationship may be provided.

Images may be generated during scanning. The ultrasound scans are used for real-time imaging. The detected radiation for one or more locations may be shown on the image, such as coloring a swath or region associated with detected radiation for a given scan (see FIG. 3 for example). The radiation information may not be imaged until a reconstruction is generated in other embodiments. The reconstruction and anatomy information are displayed to the user in real-time with the scanning.

Preoperative images may be displayed. The ultrasound or radiation information is overlaid or shown adjacent to the preoperative images.

Figure 10:
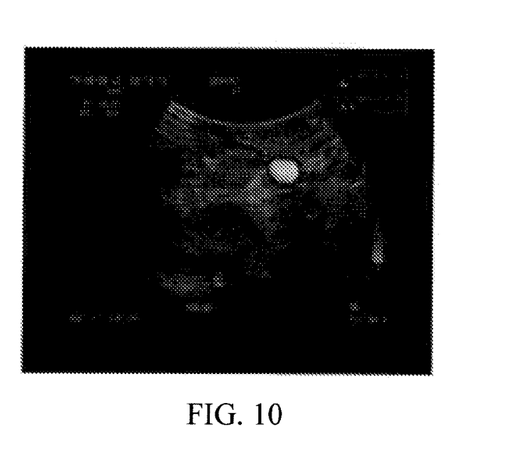
FIG. 10 is an example two-dimensional image with combined functional and anatomical information.

FIG. 10 shows an example image. The image includes anatomical information, such as an ultrasound B-mode image. The circular, lighter region represents a color or other indication of detection of nuclear information. This lighter region is formed from modulating the B-mode values, such as with a color. Alternatively, an overlay or combination is used. Based on the image formed with a handheld probe, the user may determine the locations for therapy, biopsy, or bisection. This determination is made in light of local anatomy using a handheld scanner rather than a large imaging system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A probe for multi-modal medical imaging and therapy, the probe comprising:
   an ultrasound transducer comprising a plurality of elements in an array, wherein the array comprises an N×M arrangement of elements wherein both N and M are integers greater than 1;
   a nuclear detector for detecting radiation, the nuclear detector positioned within an aperture in the N×M arrangement;
   an interconnection between the ultrasound transducer and the nuclear detector;
   a handheld housing of the ultrasound transducer, the interconnection providing common movement of the handheld housing of the ultrasound transducer and the nuclear detector during scanning by the ultrasound transducer and detection by the nuclear detector, wherein movement of the handheld housing moves the nuclear detector and interconnection;
   a processor configured to determine a motion path of the ultrasound transducer by correlating image data derived from data generated by the ultrasound transducer without using a tracking sensor;
   the processor configured to generate an image volume representing anatomy derived from data generated by the ultrasound transducer and the processor configured to generate an image representing functional information derived from data generated by the nuclear detector and the motion path, the processor further configured to direct focus a therapy transducer of the probe to perform high-intensity focused ultrasound therapy based on a location represented by the functional information integrated with the image volume.

2. The probe of claim 1 wherein the ultrasound transducer and the nuclear detector being within the handheld housing, the interconnection being fixed within the handheld housing.

3. The probe of claim 1 wherein the interconnection comprises a releasable connection.

4. The probe of claim 1 further comprising:
   a motorized wobbler connected with the nuclear detector to rock the nuclear detector at different angles relative to the ultrasound transducer during detection of the radiation.

5. The probe of claim 1 further comprising:
   a robot arm connected with the ultrasound transducer and nuclear detector.

6. The probe of claim 1 further comprising:
   a therapy transducer to perform the high-intensity focused ultrasound therapy, the interconnection connecting the therapy transducer with the ultrasound transducer and the nuclear detector.

7. The probe of claim 1 wherein the nuclear detector comprises a gamma detector.

8. The probe of claim 1 further comprising a sensor operable to track an absolute common movement of the therapy transducer and the ultrasound transducer relative to an external frame of reference, and wherein the processor is configured to generate the image as a function of the tracking of the absolute common movement.

* * * * *